United States Patent [19]

Fischer et al.

[11] Patent Number: 5,697,918

[45] Date of Patent: Dec. 16, 1997

[54] SYSTEMS FOR STORING AND DISPENSING DENTAL COMPOSITIONS

[75] Inventors: Dan E. Fischer, Sandy; David V. Fischer, West Jordan, both of Utah

[73] Assignee: Ultradent Products, Inc., South Jordan, Utah

[21] Appl. No.: 478,475

[22] Filed: Jun. 7, 1995

Related U.S. Application Data

[63] Continuation-in-part of Ser. No. 393,217, Feb. 23, 1995, abandoned.

[51] Int. Cl.$^6$ .................... A61M 5/315; A61C 5/04
[52] U.S. Cl. .................... 604/227; 604/235; 604/241; 433/90
[58] Field of Search .................... 604/57, 187, 905, 604/82–85, 93, 181, 218, 219, 227, 234, 235, 240, 241, 256, 269, 207, 407; 366/131, 337, 340; 433/80, 81, 89, 90; 141/363, 366, 357, 26, 27; 128/764, 766

[56] References Cited

U.S. PATENT DOCUMENTS

| | | |
|---|---|---|
| 3,010,705 | 11/1961 | Brown . |
| 3,729,031 | 4/1973 | Baldwin . |
| 3,757,781 | 9/1973 | Smart .................... 604/218 X |
| 4,046,145 | 9/1977 | Choksi et al. . |
| 4,351,334 | 9/1982 | Inglefield, Jr. .................... 604/227 |
| 4,551,135 | 11/1985 | Gorman et al. .................... 604/82 |
| 4,639,248 | 1/1987 | Schweblin .................... 604/187 |
| 4,743,229 | 5/1988 | Chu .................... 604/82 |
| 4,863,072 | 9/1989 | Perler . |
| 5,308,341 | 5/1994 | Chonoch .................... 604/208 |
| 5,324,273 | 6/1994 | Discko, Jr. .................... 604/240 |
| 5,425,580 | 6/1995 | Beller .................... 366/131 |

FOREIGN PATENT DOCUMENTS

| | | | |
|---|---|---|---|
| 0 242 956 | 10/1987 | European Pat. Off. .................... 604/187 |
| 1 075 282 | 2/1960 | Germany .................... 604/187 |

Primary Examiner—Michael Buiz
Assistant Examiner—A. T. Nguyen
Attorney, Agent, or Firm—Workman Nydegger Seeley

[57] ABSTRACT

A system and method for storing in bulk and readily dispensing a dental composition includes a prefilled bulk storage syringe, storage container, or squeezable tube that is capable of storing multiple doses of the composition for dispensing into a dose administration syringe. The discharge end of the bulk storage syringe, storage container, or squeezable tube can be coupled directly to the discharge end of the dose administration syringe without an adaptor, allowing the dental composition to be readily transferred directly to the dose administration syringe. The dental composition can then be readily administered to a desired area from the dose administration syringe after the bulk storage syringe, storage container, or squeezable tube has been decoupled therefrom.

25 Claims, 11 Drawing Sheets

SYSTEMS FOR STORING AND DISPENSING DENTAL COMPOSITIONS

RELATED APPLICATION

The present application is a continuation-in-part of application Ser. No. 08/393,217, entitled "Hand-Operated Syringe for Storing and Dispensing Viscous Materials," which was filed on Feb. 23, 1995, now abandoned, and which is incorporated herein by specific reference.

BACKGROUND OF THE INVENTION

1. The Field of the Invention

The present invention relates generally to systems and methods for storing and dispensing dental compositions. More particularly, the present invention is directed to hand-operated devices that are capable of storing a dental composition and dispensing the dental composition directly into a dose administration syringe for single dose administration.

2. The Relevant Technology

Medical personnel often have the need to precisely administer small amounts of gels, collagens, resinous materials, and various other liquids and materials with viscous characteristics. The storage and dispensing of these types of viscous or liquid materials presents a variety of problems. Typically, materials such as these cannot be exposed to air for even short periods of time, or they will prematurely cure and/or otherwise be contaminated. Insofar as the materials are used in various types of medical environments, they must also be kept clean. Consequently, these types of materials are often stored in bulk form within clean, air-tight canisters or bottle-like containers. Further, the containers are often sized and shaped so that the materials or compositions stored therein can be economically sold and stored in a bulk form, so as to be easily packaged and shipped.

Regardless of how suitable such storage containers are for shipping and storage, they may be entirely inappropriate for a doctor's office or dental office, or similar medical environment where the materials are to be ultimately used. In many medical and dental procedures, only a small amount of any particular material is required, and it is usually administered or applied with a small dose administration syringe. Syringes are highly favored for their ease of use and cleanliness by professionals, such as dentists, who must apply specific amounts of dental compositions to hard to reach places. Single dose administration syringes, in particular, are currently preferred by medical personnel who must avoid the risk of inadvertently transmitting diseases such as AIDS and Hepatitis B. Single dose administration syringes may be disposed of after a single use, removing the risks of improper sterilization and cross-contamination between patients.

The procedure currently preferred among dentists is to operate from trays prepared for the specific operation with all articles needed for the operation, and to dispose of everything from the tray into the trash after use. In the process of preparing such a tray, nurses or dental assistants prepare each dose administration syringe separately with the contents needed. In the process of an operation such as repairing a chipped tooth, for instance, a dentist may require the use of several syringes, each loaded with dosages of disinfectant, bonding agents, etc.

Problems arise, however, when the material must be transferred from the storage container to the dose administration syringe. As it is currently done, this process is often difficult, messy, wasteful, and inaccurate. Furthermore, it may be dangerous if the loading process provides the opportunity for cross-contamination or makes it difficult to keep the syringe clean. For example, when performing a procedure, the doctor or technician must first open the container, retrieve the necessary amount of material, and then re-seal the storage container before any of the material cures, hardens, or is otherwise contaminated. As will be appreciated, this process can be difficult, especially under the circumstances of a medically related procedure.

Further, the manner by which the material must be retrieved is also problematic. As mentioned, the material must often be transferred to a dose administration syringe of some type. One technique is to insert the discharge end of the dose administration syringe barrel into the material, and then suction the material into the syringe barrel by slowly retracting the syringe plunger. This technique, while suitable for many non-viscous liquids, is often inadequate for the retrieval of a thick, slow-flowing viscous material. Retrieval of a viscous material using this technique is slow, and it is difficult to obtain precise amounts of the material. Also, any excess amount of material that is not used in the subsequent procedure is typically discarded and wasted. Air can also be easily introduced into the syringe barrel, thereby contaminating or prematurely hardening the material. Finally, when retrieving a viscous material in this manner, it is difficult to keep the outside of the dose administration syringe clean.

An alternative approach to transferring viscous materials from a container to the administering syringe is to remove the plunger from the syringe barrel and then, by way of spoon, spatula, or similar device, transfer the material into the open end of the syringe barrel. When completed, the plunger is then reinserted into the barrel. However, this process is also slow and messy, especially where the material is tacky, sticky, or otherwise difficult to work with. Further, it is difficult to prevent air from entering the barrel and, again, the material can prematurely harden. Also, it is very difficult to transfer precise amounts of the material into the administering syringe.

Both of these techniques are wasteful in other respects as well. For instance, when the viscous material is stored within a container, it is difficult to retrieve and utilize all of the material. Much of the material can adhere to the sides and bottom of the container, or will adhere to the actual instrument being used to retrieve the material. This portion goes unused and, especially over time, can result in a large amount of waste.

An additional problem with prior syringes is that their longer length can cause users with smaller hands difficulty in gripping and maintaining control of the syringe during operation.

SUMMARY AND OBJECTS OF THE INVENTION

The present invention has been developed in response to the present state of the art and, in particular, in response to these and other problems and needs that have not been fully or completely solved by currently available devices for storing and dispensing viscous and liquid materials. Thus, it is an overall object of the present invention to provide a novel bulk storage and dispensing syringe that can be used to both store and dispense viscous and liquid materials.

It is another object of the present invention to provide a bulk storage syringe, storage container, or squeezable tube that is sized so as to be large enough to store a viscous or liquid composition in bulk form.

A further object of the present invention is to provide a bulk storage syringe that can be used to easily and efficiently dispense compositions that are viscous or liquid.

Yet another object of the present invention is to provide a bulk storage syringe that is capable of fully dispensing a viscous composition contained therein, thereby eliminating any waste of the composition.

It is also an object of the present invention to provide a bulk storage syringe, storage container, or squeezable tube that is supplied prefilled and that can provide multiple customized dosages, including unit dosing of a composition therein.

Another object of the present invention is to provide a bulk storage syringe that is sized and shaped so as to allow for the dispensing of a composition by operating the syringe with one hand.

A further object of the present invention is to provide a bulk storage syringe, storage container, or squeezable tube that can be used to dispense a precise amount of a composition contained therein directly into a dose administration syringe.

It is yet another object of the present invention to provide a bulk storage syringe that is shaped so as to be conducive to efficient packaging, storage, and handling.

An additional object of the present invention is to provide a system for storing in bulk and readily dispensing a dental composition into a dose administration syringe utilizing a bulk storage syringe, storage container, or squeezable tube coupled to the dose administration syringe without an adaptor.

Another object of the present invention is to provide a system using a bulk storage syringe, storage container, or squeezable tube in which all components placed in a patient's mouth are disposed of thereafter.

An additional object of the present invention is to provide a method for providing multiple doses of a dental composition using a bulk storage syringe, storage container, or squeezable tube.

A further object of the present invention is to provide a method of preparing and administering a single dose of a viscous or liquid composition.

Additional objects and advantages of the invention will be set forth in the description which follows and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and described herein, the present invention is directed to systems and methods for storing in bulk and readily dispensing a dental composition that can be a viscous or liquid material. In one embodiment, the system includes a prefilled bulk storage syringe comprising a storage barrel having an inlet end and a discharge end, a storage plunger slidably disposed within the storage barrel, and a gripping means arcuately disposed on the storage barrel in essentially a semicircle around a portion of the barrel. The gripping means forms a platform means upon which all finger tips except the thumb of a user's hand can rest while the storage plunger is being advanced within the storage barrel so as to dispense the dental composition. A predetermined distance between the gripping means and the inlet end of the storage barrel allows the fingers of a user to remain in substantial abduction while the storage plunger is advanced toward the discharge end of the storage barrel.

The storage barrel of the bulk storage syringe is preferably oversized so that it can be used to store multiple doses of a dental composition in a bulk form. The gripping means can retain a plurality of fingers of one hand, while the palm of the same hand is simultaneously received and seated on a plunger handle means, which is disposed on the end of the storage plunger. This arrangement provides for a one-handed, yet leveraged and comfortably controlled, operation of the bulk storage syringe so that even the most viscous material can be expressed easily, efficiently, and precisely. Advantageously, the gripping means is not disposed around the entire storage barrel, but is adapted so as to be fitted partially around the circumference of the barrel. In this way, the gripping means preferably forms a flat surface that is coextensive with a portion of the outer surface of the storage barrel. This allows the bulk storage syringe to be laid flat without rolling, and to be easily packaged, especially in conjunction with other bulk storage syringes.

The system of the invention also includes a dose administration syringe comprising a dose barrel having a discharge end, a dose plunger slidably disposed within the dose barrel, and means for coupling the discharge end of the bulk storage syringe to the discharge end of the dose administration syringe. This allows the bulk storage syringe and the dose administration syringe to be coupled without an adaptor and to be in fluid communication with each other for dispensing a single dose of the dental composition from the bulk storage syringe into the dose administration syringe.

Prior to a medical or dental procedure, the bulk storage syringe can be used to transfer a specific amount of a composition directly to the dose administration syringe, which is afterwards used in the particular medical or dental procedure and then disposed of. By transferring the stored composition directly to the dose administration syringe, the composition is not exposed to air or other contaminants, and is therefore maintained in a clean and non-cured state. Further, because of the bulk storage syringe's design, a precise amount of the required material can be easily and accurately transferred to the dose administration syringe, thereby reducing the need to discard unused portions.

In an alternative embodiment of the system of the present invention, the bulk storage syringe is replaced with a prefilled bulk storage container that includes a storage barrel having a discharge end, and a diaphragm slidably disposed within the storage barrel. The discharge end of the storage container can be coupled directly to the discharge end of a dose administration syringe without an adaptor. This allows the storage container and the dose administration syringe to be in fluid communication with each other so that a single dose of the composition can be drawn from the storage container into the dose administration syringe.

In a further embodiment, a prefilled bulk storage squeezable tube can be used in place of the bulk storage syringe described above. The squeezable tube includes a barrel portion having a discharge end that can be coupled directly to the discharge end of a dose administration syringe without an adaptor. This allows the squeezable tube and the dose administration syringe to be in fluid communication with each other for dispensing a single dose of the composition from the squeezable tube into the syringe.

A method for providing multiple doses of a dental composition using the hand-operated bulk storage syringe, storage container, or squeezable tube is also part of the present invention and comprises the following procedure. First, the bulk storage syringe, storage container, or squeezable tube are supplied prefilled with bulk amounts of a desired composition. The dose administration syringe is also supplied having the features described above. When it becomes necessary to administer the composition to a patient, the discharge end of the bulk storage syringe, storage container, or squeezable tube is coupled to the discharge end of the dose administration syringe. A single dose of the composition is then expressed or transferred to the dose administration syringe. The bulk storage syringe, storage container, or squeezable tube is then disengaged from the dose administration syringe and the dose of the composition is administered with the dose administration syringe to a patient. The dose administration syringe is then disposed of, eliminating any chance of cross-contamination between patients.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof, which are illustrated in the appended drawings. Understanding that these drawings depict only typical embodiments of the invention and are, therefore, not to be considered limiting of its scope, the invention and the presently understood best mode for making and using the same will be described with additional specificity and detail through the use of the accompanying drawings in which.

DETAILED DESCRIPTION OF THE PREFERRED EMBODIMENTS

The present invention is directed to systems and methods for storing in bulk and readily dispensing a dental composition into a dose administration syringe utilizing a bulk storage syringe, a bulk storage container, or a bulk storage squeezable tube. Each of these components will be described in detail below referring to FIGS. 1–13.

Figure 1:
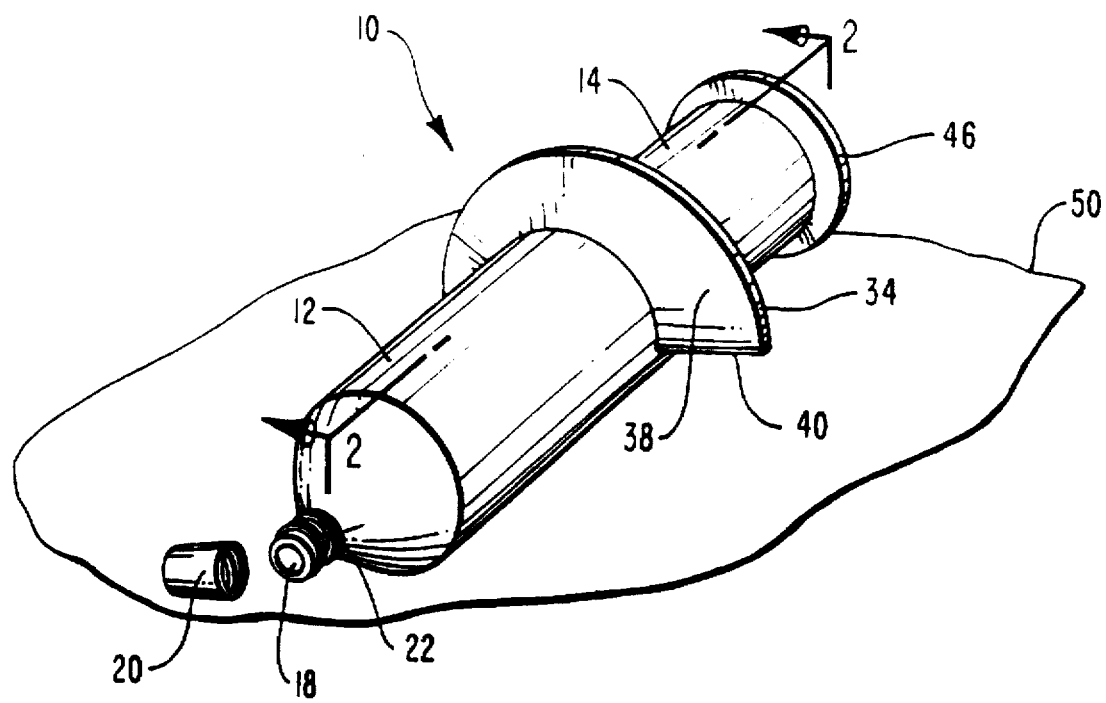
FIG. 1 is a perspective view of the hand-operated bulk storage and dispensing syringe of the present invention, resting on a flat surface.

A hand-operated bulk storage and dispensing syringe, designated generally at 10, is shown in FIG. 1. Bulk storage syringe 10 includes an oversized storage barrel 12, and a correspondingly sized storage plunger 14. Storage barrel 12 and storage plunger 14 are both preferably constructed from a plastic material, such as polypropylene or similar plastics, so that storage syringe 10 is sufficiently rigid for storing and expressing viscous or liquid materials.

As used herein, the term "viscous material" or "viscous composition" is intended to mean any type of flowable material or composition that is thicker than water. The term "liquid material" or "liquid composition" is intended to mean any type of flowable material or composition that has about the same consistency as water.

Figure 2:
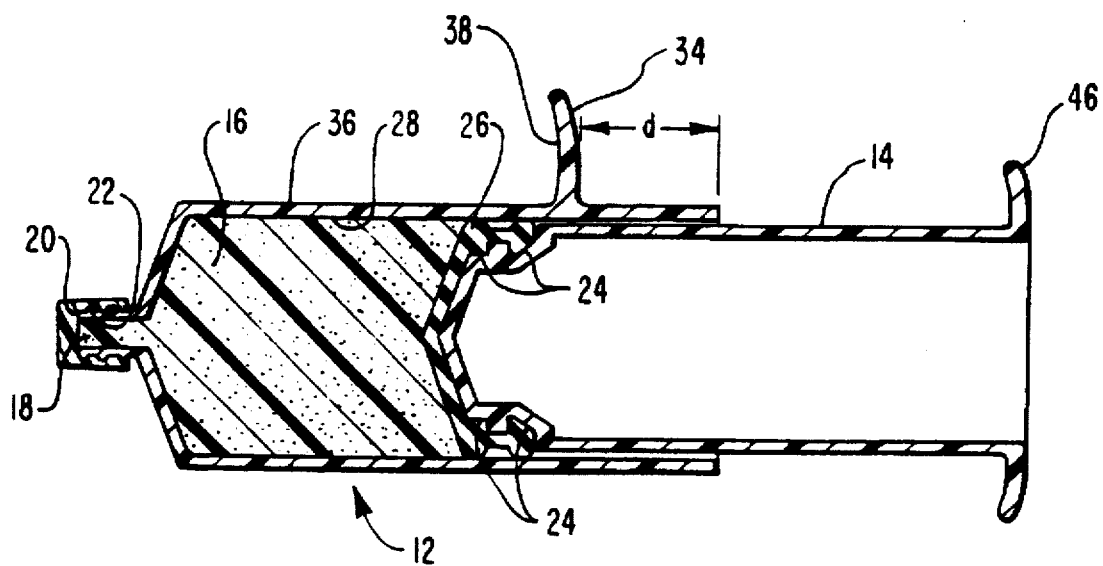
FIG. 2 is a cross-sectional view of the bulk storage syringe in FIG. 1, taken along lines 2—2.

As shown in FIG. 2, storage plunger 14 is slidingly received within storage barrel 12, and is used for pushing a viscous or liquid composition 16, such as a dental composition contained within barrel 12 through an open discharge end 18 formed at the end of barrel 12. Formed at the tip of storage plunger 14 is a molded channel 24 for receiving an elastomeric tip 26 or similar sealing device which forms a slidable, yet air-tight seal with an inner surface 28 of storage barrel 12. The elastomeric tip 26 insures that composition 16 is completely discharged when plunger 14 is fully advanced in barrel 12, thereby eliminating any waste of composition 16. The elastomeric tip 26 also helps to create an air-tight seal within barrel 12 when bulk storage syringe 10 is being used as a storage device.

Storage barrel 12 has a cylindrical shape, and is large enough such that multiple doses of composition 16 can be stored in bulk form therein. Preferably, barrel 12 has a diameter of at least about one inch, but it will be appreciated that barrel 12 could be of varying dimensions, depending on the bulk amount of material that is to be stored. As is further shown in FIGS. 1 and 2, when being used as a storage device, plunger 14 remains within barrel 12 in a partially retracted position, and a storage cap 20 is threadably attached to a threaded portion 22 formed on the exterior of discharge end 18. In this way, the interior of barrel 12 is maintained air-tight, thereby insuring that composition 16 contained therein does not prematurely cure or otherwise become contaminated.

Figure 3:
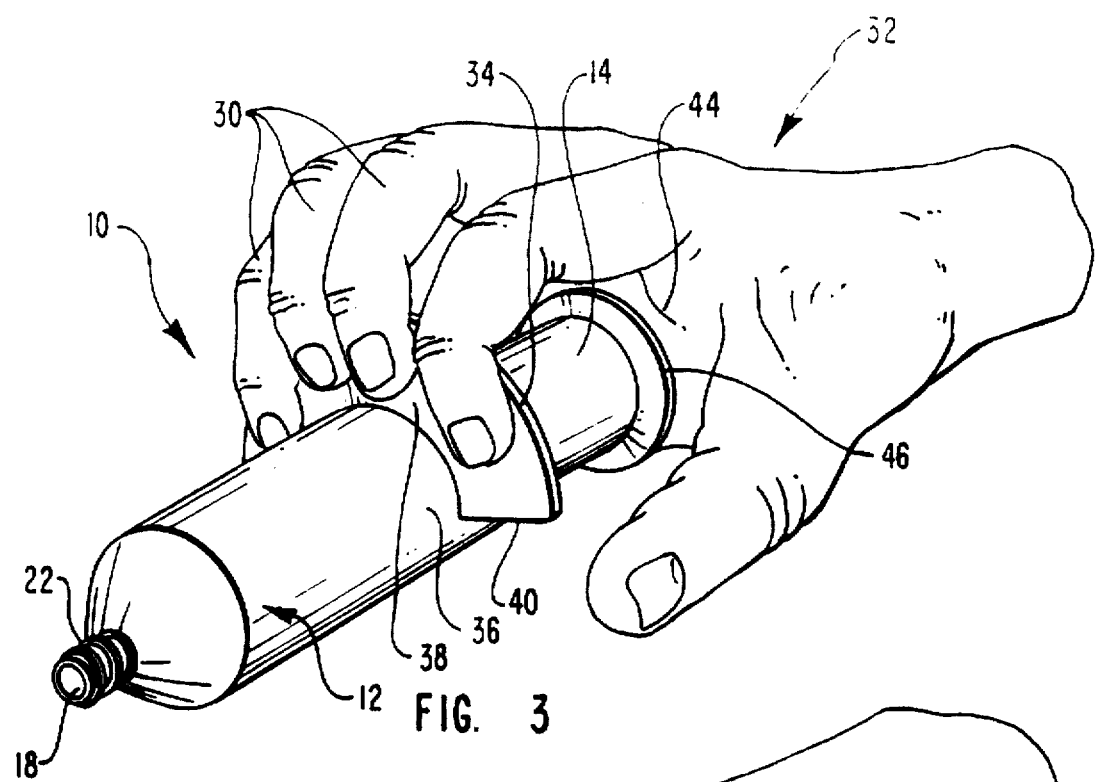
FIG. 3 is a perspective view of the bulk storage syringe in FIG. 1 being operated in one preferred manner.

Referring now to FIG. 3, storage syringe 10 further includes a barrel gripping means, arcuately disposed on storage barrel 12 in essentially a semicircle, for retaining a plurality of fingers 30 of one hand 32 while plunger 14 is being advanced within barrel 12 to dispense a viscous or liquid dental composition from discharge end 18. The gripping means forms a platform means upon which all finger tips except the thumb of a user's hand can rest, as illustrated in FIG. 3. By way of illustration and not limitation, in a presently preferred embodiment, the gripping means is comprised of a finger flange 34, which is continuous and extends radially outwardly from a surface 36 of barrel 12 in a substantially perpendicular manner. The platform means comprises in a preferred embodiment a single and continuous finger retaining surface 38, which permits several fingers of one hand to be positioned in an adjacent manner. Preferably, finger retaining surface 38 is slightly curved to form a convex shelf, as best shown in FIG. 2, so that finger retaining surface 38 can better accommodate and retain the plurality of fingers 30 that are positioned thereon. It should be understood that other equivalent structures performing substantially the same functions as the recited structure for the gripping means and the platform means are within the scope of the present invention. For example, the finger flange could be discontinuous and the finger retaining surface could be flat instead of curved or convex.

A predetermined distance between the gripping means and the inlet end of storage barrel 12 allows the fingers of a user to remain in substantial abduction while plunger 14 is advanced toward discharge end 18 of storage barrel 12. As shown in FIG. 2, finger flange 34 is located a predetermined distance "d" from the inlet end of barrel 12, opposite discharge end 18. This arrangement provides greater leverage as well as a more comfortable grip, making it easier to dispense the contents of storage syringe 10. In a presently preferred embodiment, predetermined distance "d" is about 0.5 to about 1.5 inches in length. Thus, even when plunger 14 is fully inserted into barrel 12, there is adequate separation between the fingers and the palm of the hand so that the average person has sufficient leverage to exert an appreciable amount of pressure between finger retaining surface 38 and plunger 14, and can maintain a comfortable grip.

Bulk storage syringe 10 has been designed from an ergonomic standpoint to allow the most comfortable position of a hand operating the syringe with multiple fingers. The starting point for the operation of storage syringe 10 is at abduction of fingers 30, which is the curved position of the fingers when the hand is in a generally relaxed position. The abduction position of fingers 30 of hand 32 is shown in FIG. 3. Thus, hand 32 does not need to be fully extended to obtain a grip on storage syringe 10 before expression of material thereout, even by operators with smaller hands. The design of storage syringe 10 in having predetermined distance d between finger flange 34 and the inlet end to storage barrel 12 also allows plunger 14 to be inserted completely into barrel 12 while the fingers are in substantial abduction without totally contracting hand 32. During unit dosing using storage syringe 10, plunger 14 is pushed only partially into barrel 12 for a given dose, during which the fingers of the operator are in the comfortable abduction position.

Figure 4:
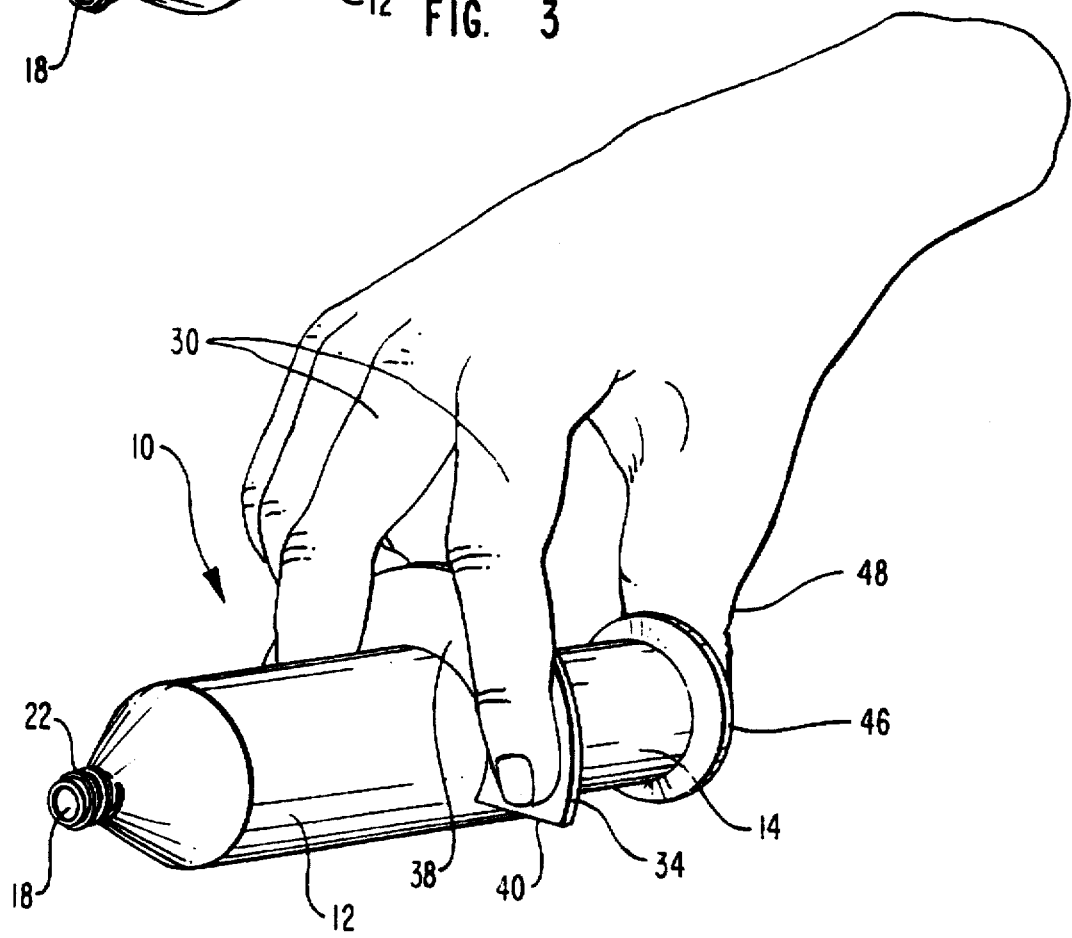
FIG. 4 is a perspective view of the bulk storage syringe in FIG. 1 being operated in another preferred manner.
Figure 5:
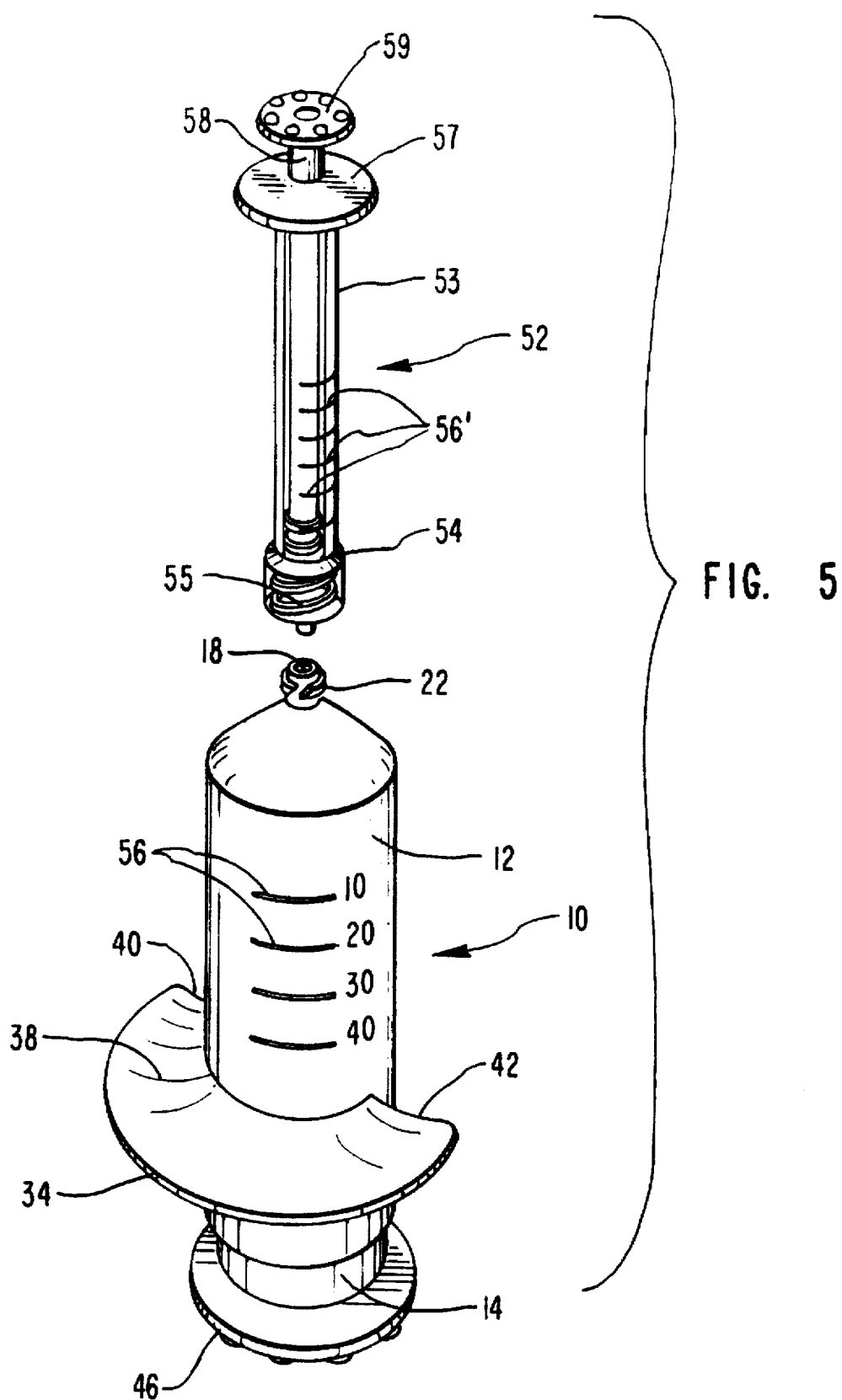
FIG. 5 is a perspective view of the bulk storage syringe of FIG. 1 and a dose administration syringe used in a system for storing and dispensing a dental composition.
Figure 6:
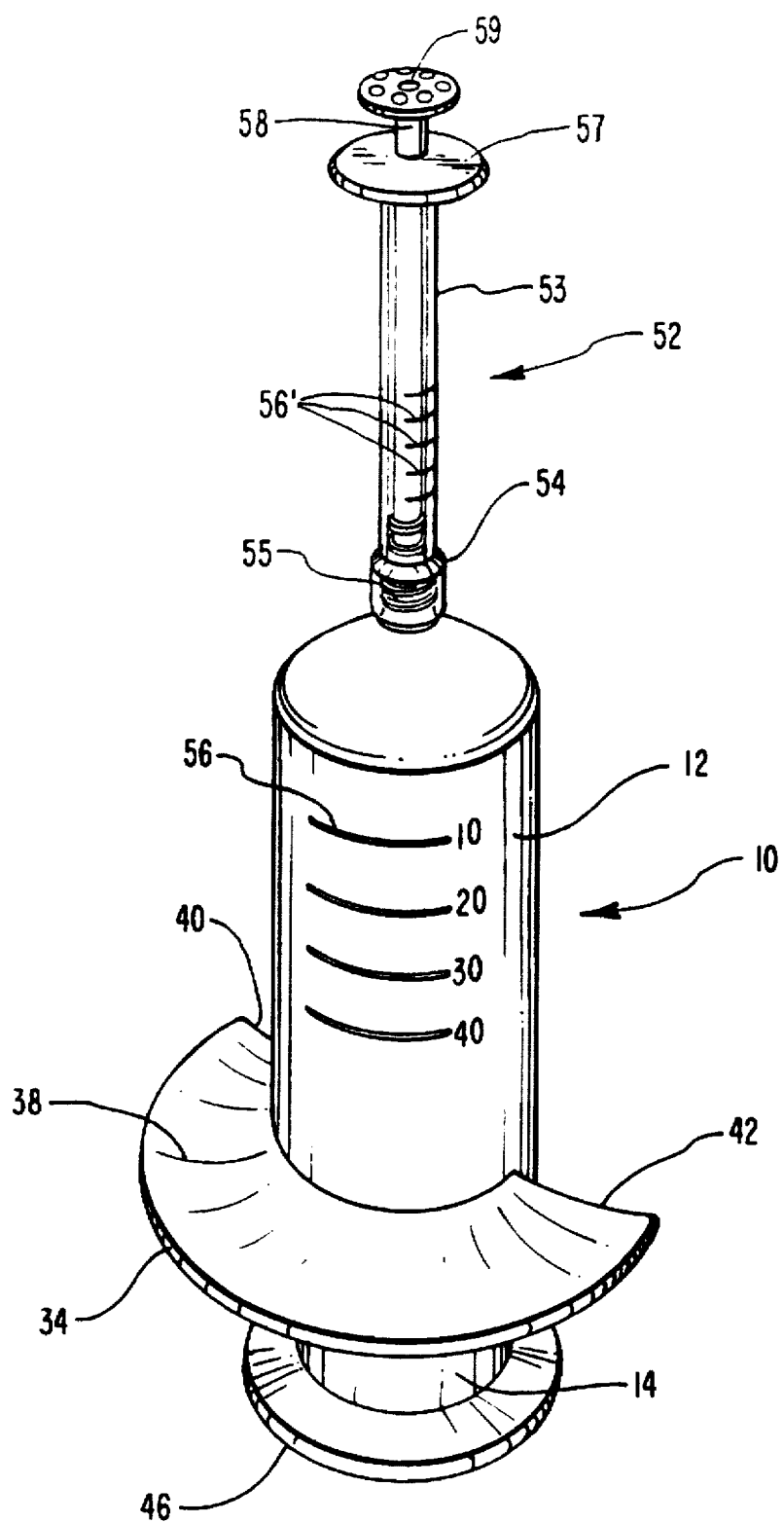
FIG. 6 is a perspective view of the bulk storage syringe of FIG. 1 operatively coupled to the dose administration syringe shown in FIG. 5.

Importantly, finger flange 34 does not extend around the entire circumference of storage barrel 12. Rather, finger flange 34 extends only partially around barrel 12, as is shown in FIGS. 1 and 3–6. Preferably, finger retaining surface 38 is capable of receiving the four fingers of one hand in an adjacent manner. Because finger flange 34 extends only partially around the outer periphery of barrel 12, finger flange 34 preferably has a first lateral edge 40 and a second lateral edge 42 formed at both ends, as is best illustrated in FIGS. 5 and 6. The first and second lateral edges 40, 42 are both substantially flat, and together form a flat surface. As shown in FIG. 1, this prevents storage syringe 10 from rolling when placed on a support surface 50. Further, since storage syringe 10 can be laid flat, it is much more conducive to being efficiently and compactly packaged with other like syringes.

Storage syringe 10 further includes a plunger handle means that is formed on the end of storage plunger 14 and which is for receiving and seating against palm 44 of hand 32 while the plurality of fingers 30 are simultaneously retained by finger retaining surface 38 of finger flange 34 as shown in FIG. 3. One presently preferred embodiment of the plunger handle means is shown as comprising, for example, a circular flange 46 formed at the rear end of plunger 14. As can be seen in FIG. 3, circular flange 46 is concentric with plunger 14, and is sized so as to be capable of being comfortably received and seated within the palm of hand 32 while fingers 30 are simultaneously retained by finger retaining surface 38 of finger flange 34. As FIG. 3 illustrates, this arrangement allows syringe 10 to be held in one hand, such that a compressive force exerted by fingers 30 toward palm 44 results in plunger 14 being advanced within barrel 12.

As will be appreciated, this arrangement provides the leverage that is required to easily and accurately dispense viscous materials. For materials having a lower viscosity, and thereby requiring less force to be dispensed from storage barrel 12, storage syringe 10 also allows for a different mode of operation. As shown in FIG. 4, two fingers 30 can be positioned on finger retaining surface 38 of finger flange 34, and plunger 14 advanced by placing thumb 48 on circular flange 46. The thumb 48 is then used to advance plunger 14, and dispense material from within barrel 12 through discharge end 18.

Figure 7:
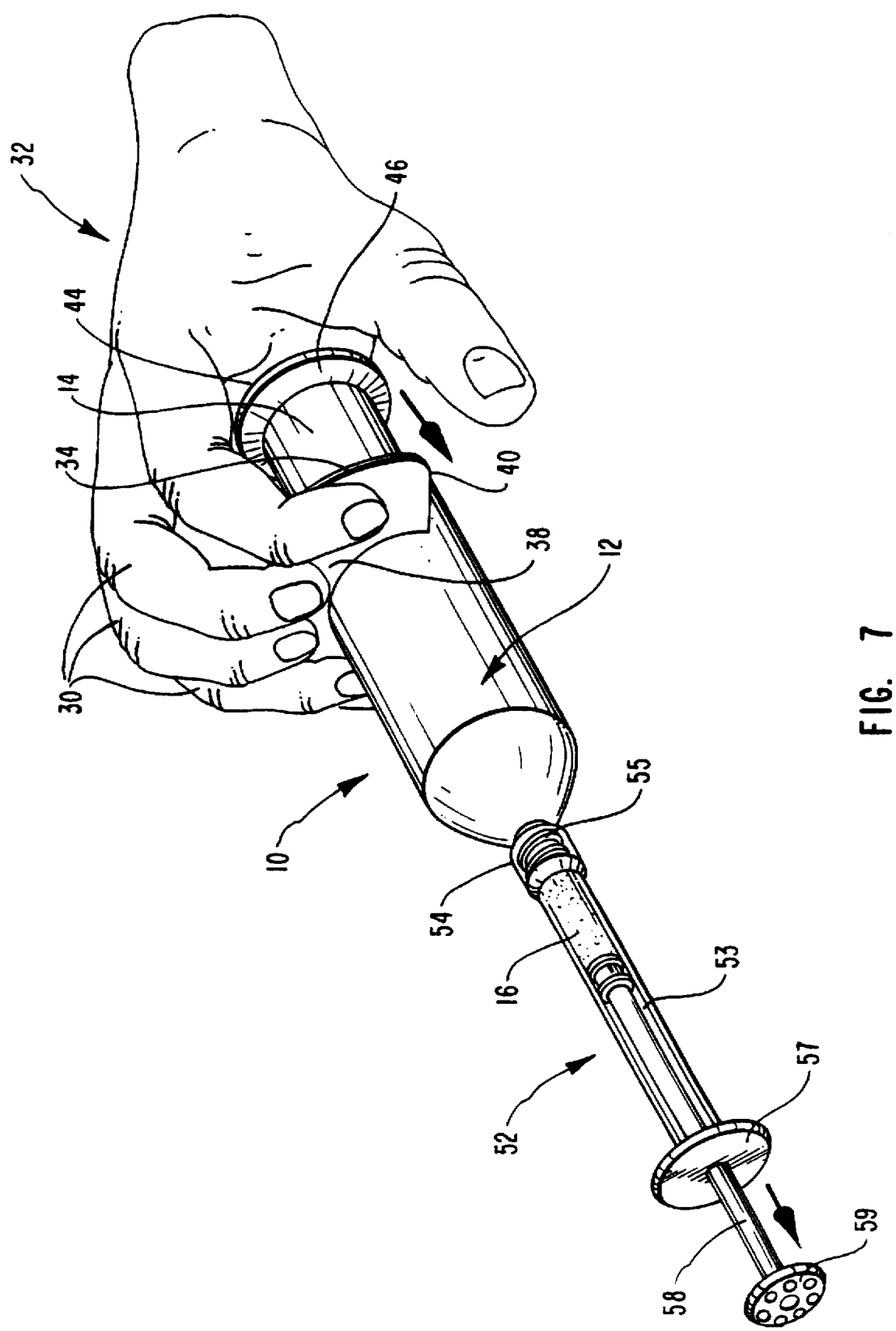
FIG. 7 is a perspective view of the bulk storage syringe and dose administration syringe shown in FIG. 6 being operated in a preferred manner for dispensing a dental composition into the dose administration syringe.

Referring to FIGS. 5–7, a first embodiment of the system for storing and dispensing a dental composition is illustrated utilizing storage syringe 10 and a dose administration syringe 52. As illustrated in FIGS. 5 and 6, dose administration syringe 52 has a dose barrel 53 having a discharge end 54. Dose administration syringe 52 also includes a finger flange 57, and a dose plunger 58 slidably disposed in dose barrel 53. A thumb flange 59 is disposed on the end of plunger 58 for supporting the thumb of a user during administration of a dose. Either storage syringe 10 or dose administration syringe 52 may be marked with gradient indicators 56 and 56' to further aid in dispensing a precise amount of material such as a single dosage to dose administration syringe 52.

A means for detachably coupling storage syringe 10 to dose administration syringe 52 is also provided. One presently preferred embodiment of this coupling means comprises a threaded portion 22 formed of male threads on the exterior surface of discharge end 18 of storage syringe 10. Threaded portion 22 is formed so as to couple with a complementary threaded portion 55 formed with female threads in discharge end 54 of dose administration syringe 52. This allows storage syringe 10 and dose administration syringe 52 to be coupled without the use of an adaptor as shown in FIG. 6.

It will be appreciated that the coupling means can be implemented using various other equivalent structures and be within the intended scope of the invention. For instance, dose administration syringe 52 could be detachably coupled to bulk storage syringe 10 by way of a Luer-lock type attachment in which one syringe, preferably storage syringe 10, would utilize a male Luer connector, and the other syringe would utilize a female Luer connector. Other arrangements that could be used include a releasable snap attachment and any similar arrangement wherein dose administration syringe 52 detachably couples to discharge end 18 of storage syringe 10.

As shown in FIG. 7, composition 16 contained within storage syringe 10 can be dispensed into the detachably coupled dose administration syringe 52 by advancing plunger 14 into barrel 12. The dose is transferred by gripping finger flange 34 with up to four fingers 30 of one hand 32, while circular flange 46 of plunger 14 is seated in the palm 44 of hand 32. Using this arrangement, composition 16 can be transferred readily and comparatively effortlessly. This arrangement also facilitates manipulation and operation of storage syringe 10 with a single hand. The dose administration syringe 52 can then be detached and storage cap 20 reattached to threaded portion 22 of storage syringe 10. The dose administration syringe 52 can then be used for the specific medical or dental procedure and afterwards disposed of. As will be appreciated, dose administration syringe 52 can be any type of syringe that is used in connection with the application and administration of viscous or liquid materials.

The bulk storage syringe used in the systems and methods of the invention is oversized, and is thereby capable of storing bulk amounts of a composition. Further, the novel shape of the bulk storage syringe allows for its packaging and storing, together with other like syringes, in an organized, space-saving, and efficient manner. Not only does the bulk storage syringe act as a storage device, it also allows for easy and efficient dispensing of viscous or liquid compositions contained therein. The novel design of the bulk storage syringe aids in convenient and efficient operation by providing an optimal hand position, which provides the leverage needed to express viscous compositions, as well as improved ergonomics in providing a comfortable gripping position. The ability to couple a dose administration syringe to the bulk storage syringe advantageously allows a precise amount of a composition to be dispensed into the dose administration syringe quickly and safely, without danger of being exposed to air or other contaminants, and in a manner that reduces waste. The corresponding method allows for the convenient use of an easily fillable single dose administration syringe that is disposed of after use for maximum safety.

Figure 8:
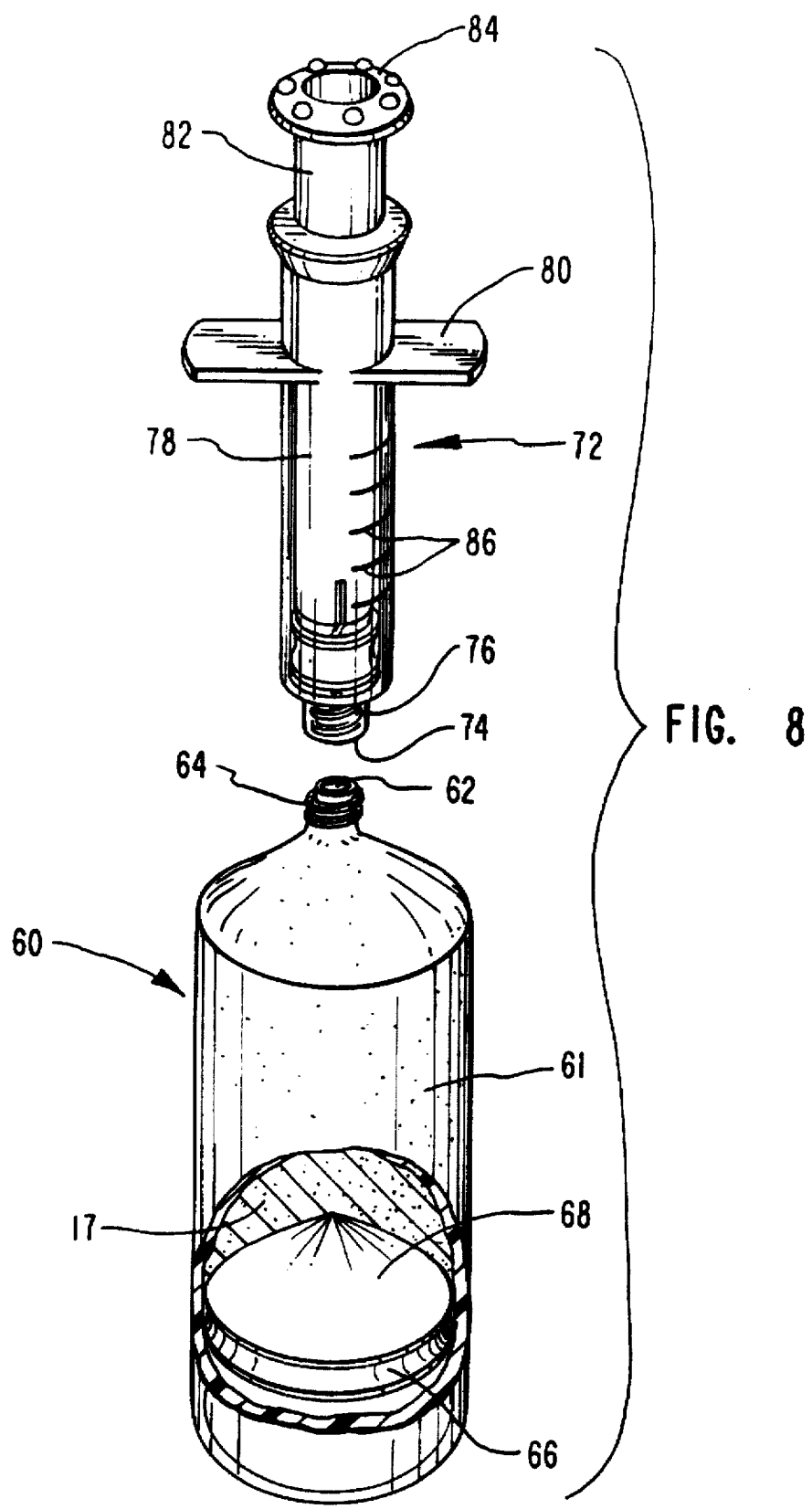
FIG. 8 is a perspective view of a storage container and a dose administration syringe used in a system for storing and dispensing a dental composition.
Figure 9:
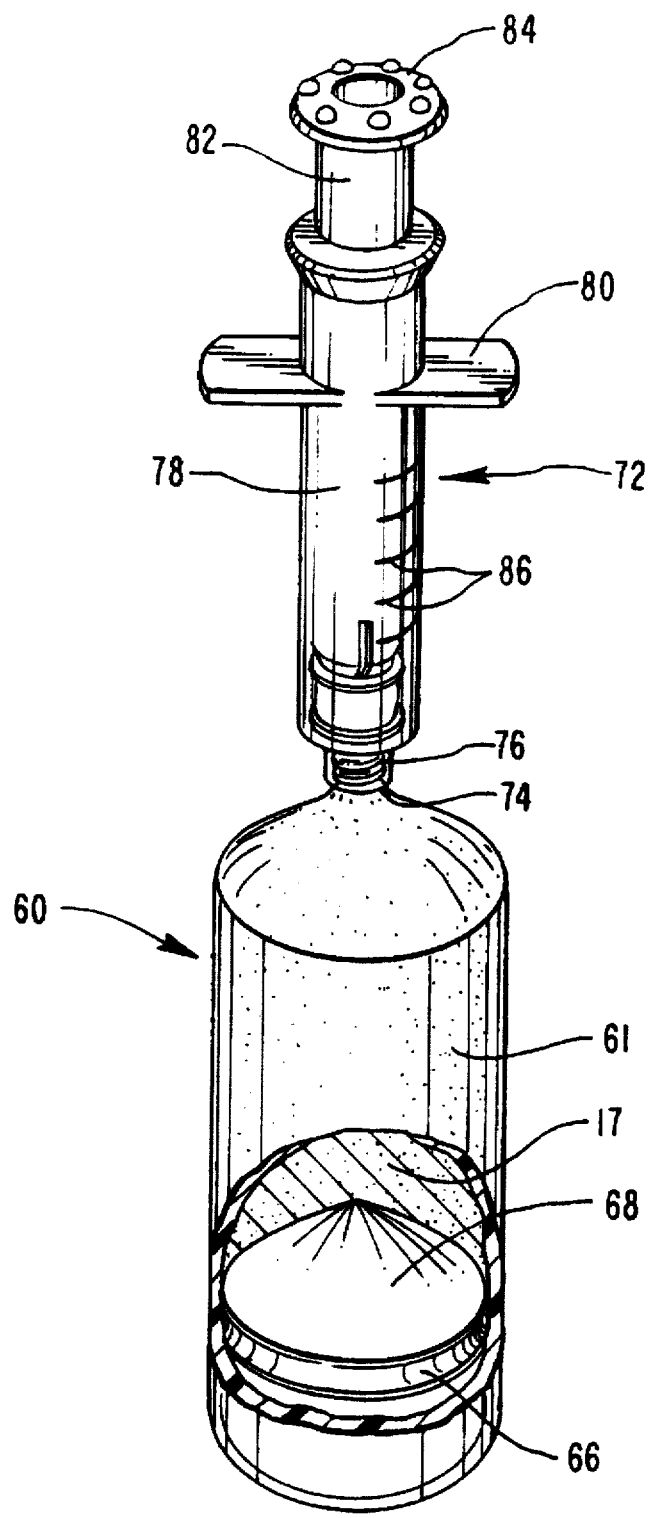
FIG. 9 is a perspective view of the storage container operatively coupled to the dose administration syringe shown in FIG. 8.
Figure 10:
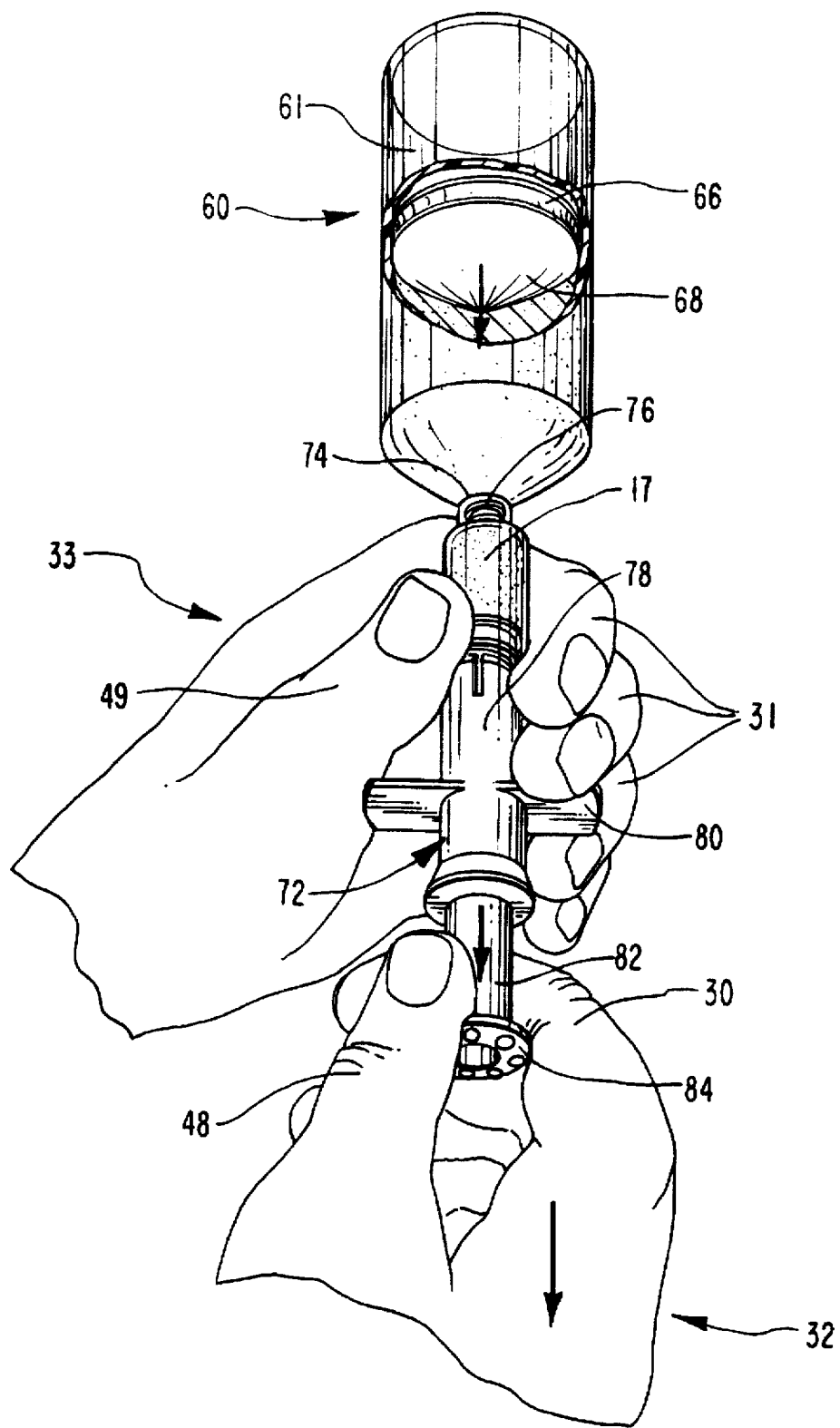
FIG. 10 is a perspective view of the storage container and dose administration syringe shown in FIG. 9 being operated in a preferred manner for drawing a dental composition into the dose administration syringe.

An alternative embodiment of the system for storing and dispensing a dental composition according to the invention is shown in FIGS. 8–10. A bulk storage container or vial 60, which is sized to store a dental composition 17 in bulk form, has an outer surface 61 and a discharge end 62. A diaphragm 66 is disposed within storage container 60 for providing an airtight seal for the inlet end of storage container 60. An elastomeric tip 68, preferably of conical shape, protrudes inwardly from diaphragm 66 in order to allow complete discharge of composition 17 disposed in storage container 60.

A dose administration syringe 72 is provided for attachment to storage container 60 as illustrated in FIGS. 8–9. Dose administration syringe 72 includes a dose barrel 78 having a discharge end 74 and a finger flange 80 protruding from dose barrel 78. A dose plunger 82 is disposed within dose barrel 78, and dose plunger 82 has a thumb flange 84 at the outer end thereof. Thumb flange 84 supports the thumb of a user during administering of a dose of composition 17. Dose administration syringe 72 can be provided with gradient indicators 86 on dose barrel 78 to aid in dispensing a precise amount of composition 17 into dose administration syringe 72.

A means for detachably coupling storage container 60 to dose administration syringe 72 is also provided. One presently preferred embodiment of this coupling means comprises a threaded portion 64 formed of male threads on the exterior surface of discharge end 62 of storage container 60 as shown in FIG. 8. Threaded portion 64 is formed so as to couple with a complementary threaded portion 76 formed with female threads in discharge end 74 of dose administration syringe 72. This allows storage container 60 and dose administration syringe 72 to be coupled without the use of an adaptor as shown in FIG. 9.

It will be appreciated that the coupling means can be implemented using various other equivalent structures and be within the intended scope of the invention. For example, dose administration syringe 72 can be detachably coupled to storage container 60 by way of a Luer-lock type attachment in which storage container 60 would utilize a male Luer connector, and dose administration syringe 72 would utilize a female Luer connector. Other arrangements that could be used include a releasable snap attachment and any similar arrangement wherein dose administration syringe 72 detachably couples to discharge end 62 of storage container 60.

A preferred manner of operation for dispensing a dental composition 17 from storage container 60 into dose administration syringe 72 is shown in FIG. 10. Dose administration syringe 72 can be grasped with fingers 30, 31 and thumbs 48, 49 of hands 32, 33 in the manner shown. Dose plunger 82 is pulled outwardly from dose barrel 78 by hand 32, thereby drawing composition 17 from storage container 60 into dose barrel 78 of dose administration syringe 72. As composition 17 is drawn from storage container 60, diaphragm 66 moves inwardly as shown in FIG. 10 thereby keeping an airtight seal in storage container 60.

Figure 11:
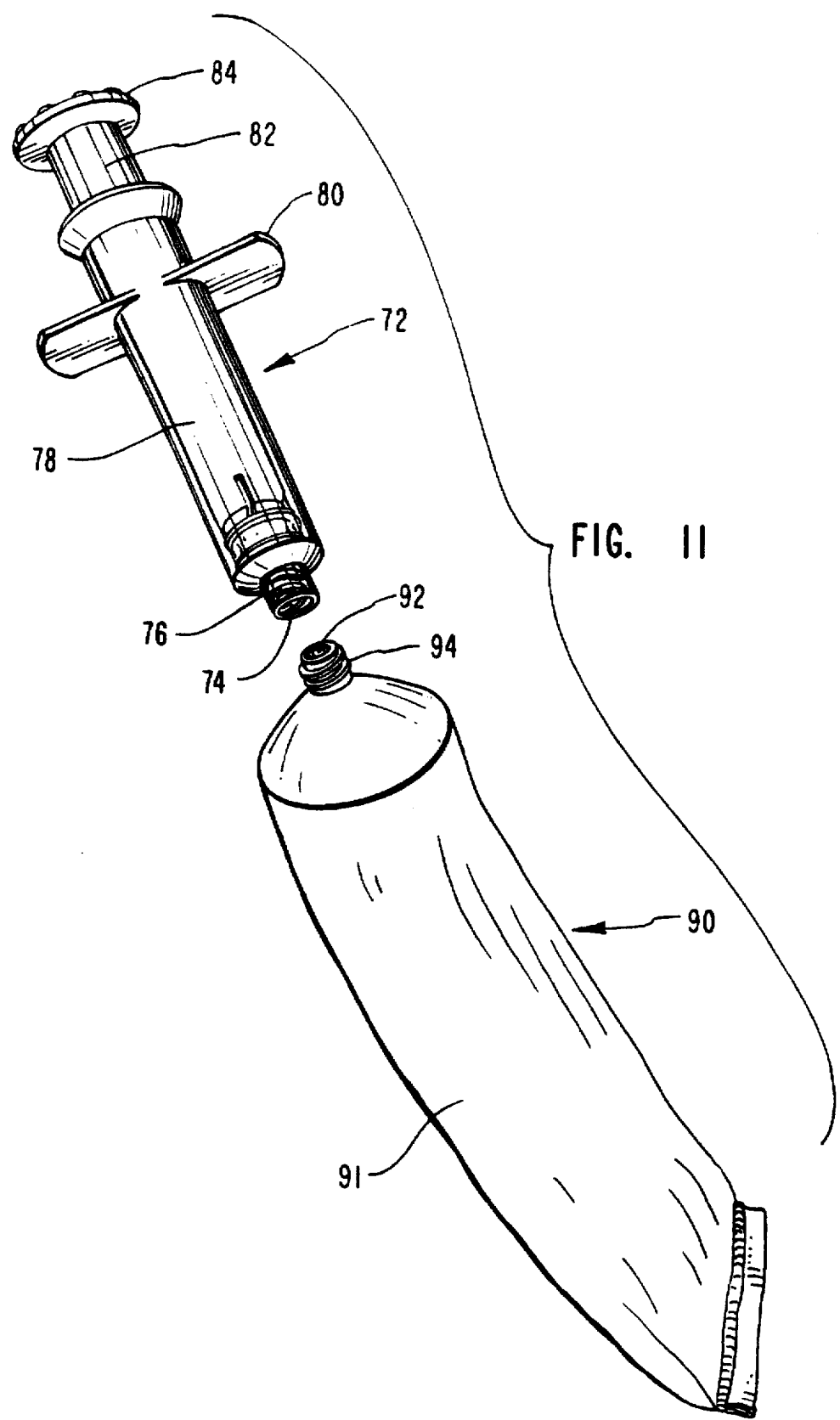
FIG. 11 is a perspective view of a squeezable tube and a dose administration syringe used in a system for storing and dispensing a dental composition.
Figure 12:
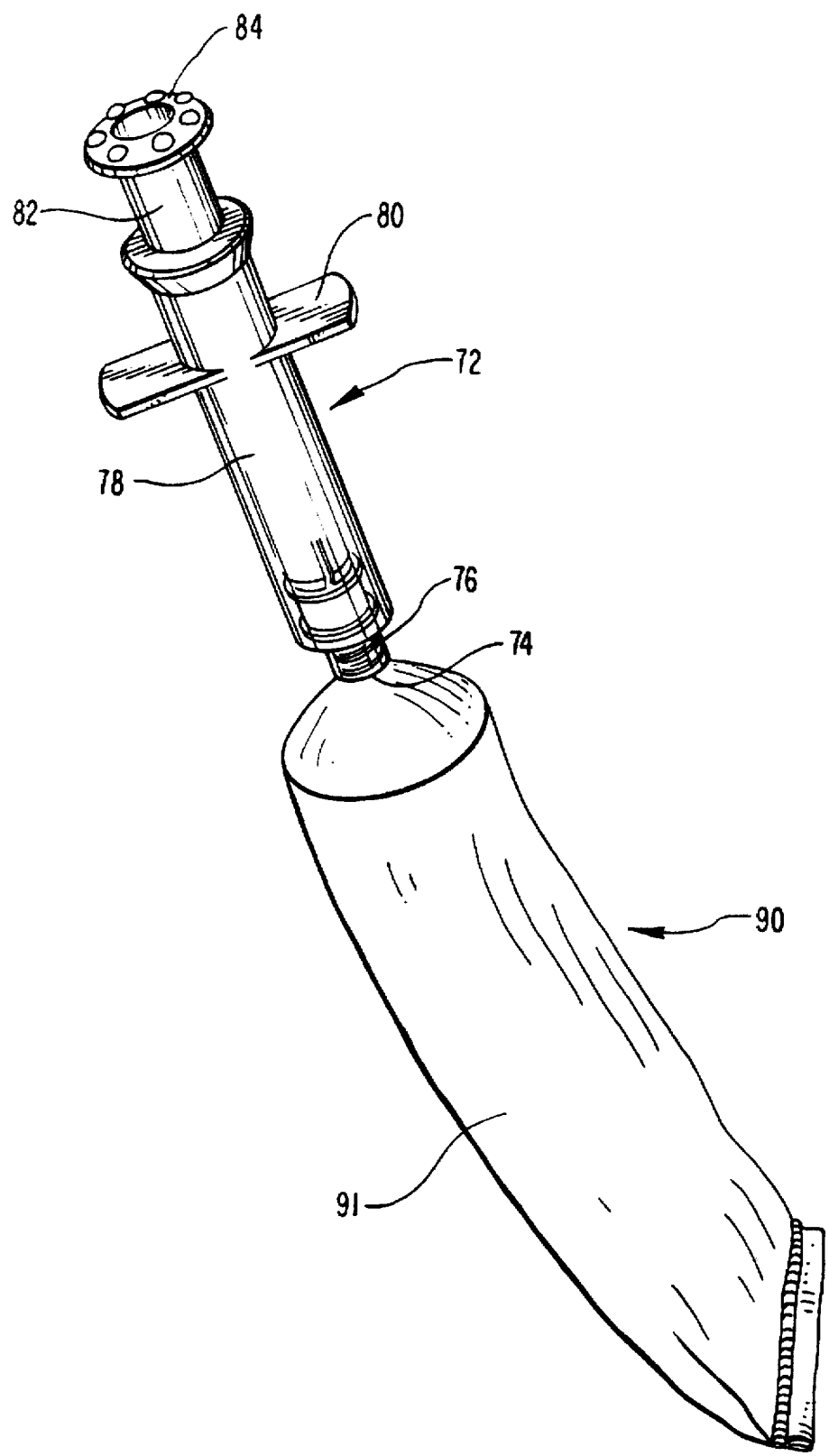
FIG. 12 is a perspective view of the squeezable tube operatively coupled to the dose administration syringe shown in FIG. 11.
Figure 13:
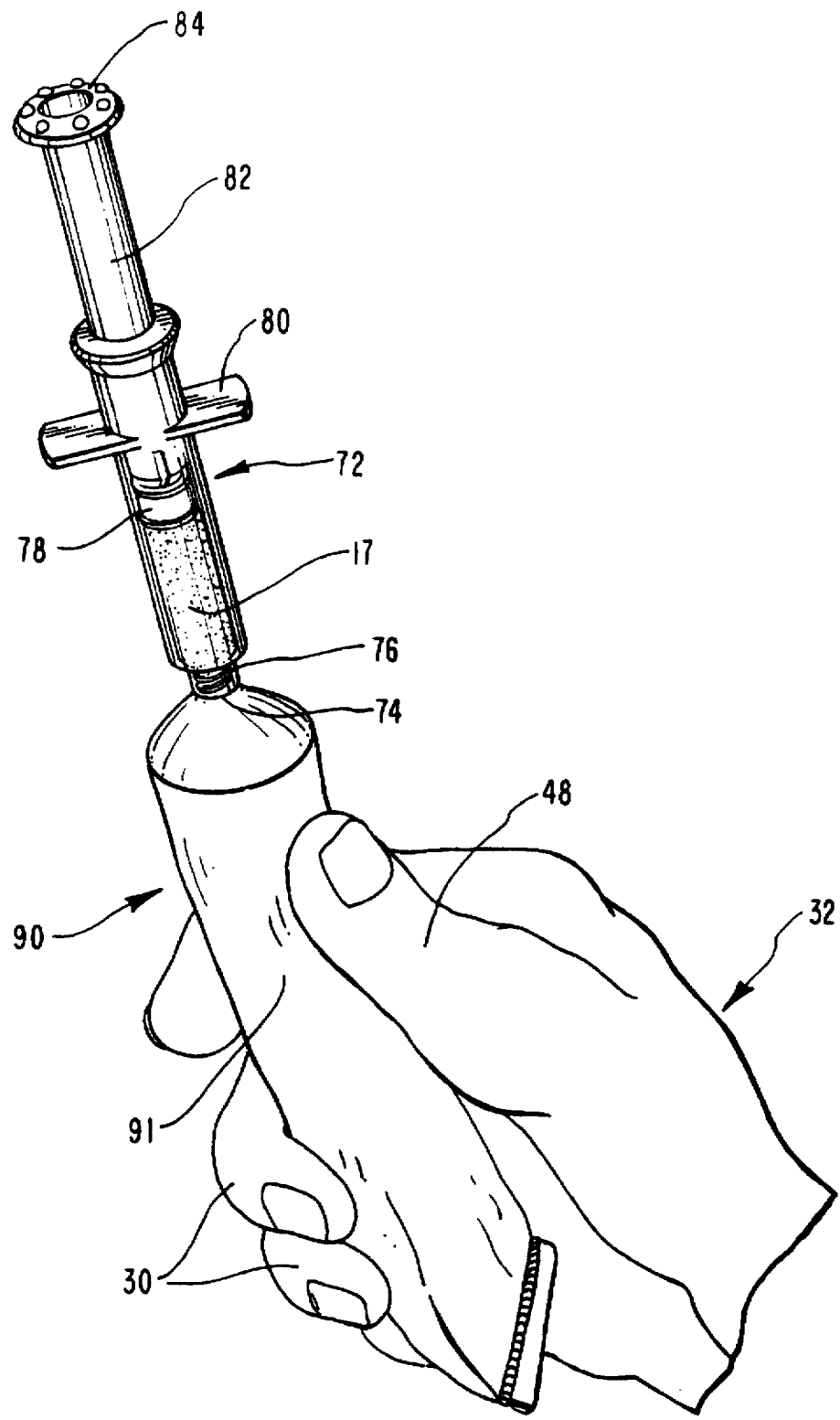
FIG. 13 is a perspective view of the squeezable tube and dose administration syringe shown in FIG. 12 being operated in a preferred manner to dispense the dental composition into the dose administration syringe.

An additional embodiment of the system for storing and dispensing a dental composition according to the invention is illustrated in FIGS. 11–13. A bulk storage squeezable tube 90, which is sized for storing dental composition 17 in bulk form, has an outer surface 91 and a discharge end 92. Dose administration syringe 72 described above is provided for attachment to squeezable tube 90.

A means for detachably coupling squeezable tube 90 to dose administration syringe 72 is also provided. One presently preferred embodiment of this coupling means comprises a threaded portion 94 formed of male threads on the exterior surface of discharge end 92 of squeezable tube 90 as shown in FIG. 11. Threaded portion 94 is formed so as to couple with a complementary threaded portion 76 formed with female threads in discharge end 74 of dose administration syringe 72. This allows squeezable tube 90 and dose administration syringe 72 to be coupled without the use of an adaptor as shown in FIG. 12. The coupling means can be implemented using various other equivalent structures and be within the intended scope of the invention. For example, dose administration syringe 72 could be detachably coupled to squeezable tube 90 by way of a Luer-lock type attachment as discussed above, as well as by other attaching mechanisms.

FIG. 13 shows a preferred manner for dispensing composition 17 into dose administration syringe 72. Hand 32 squeezes outer surface 91 by compressing squeezable tube 90 between thumb 48 and fingers 30. This compression of squeezable tube 90 forces composition 17 into dose barrel 78 of dose administration syringe 72. Squeezable tube 90 is compressed for the length of time necessary to dispense a desired dosage into dose administration syringe 72.

A method for providing multiple doses of a dental composition, and of preparing and administering a single dose of the composition is also part of the present invention. As a first step in the method, the bulk storage syringe, storage container, or squeezable tube as described above is supplied to the dentist, medical professional, or other user, prefilled with bulk amounts of the desired composition, which enable multiple customized dosages to be obtained therefrom, including unit dosing of the composition. The dose administration syringe as described above is also supplied. The composition may then be stored until a dose is needed to be administered to a patient. To prepare the dose, the storage cap is removed and the discharge end of the bulk storage syringe, storage container, or squeezable tube is coupled to the discharge end of the dose administration syringe. A single dose of the composition to be administered is then expressed or transferred to the dose administration syringe. The amount of the dose can be measured using either gradients on the bulk storage syringe, or gradients on the dose administration syringe.

Once the dose has been transferred, the dose administration syringe is uncoupled from the bulk storage syringe, storage container, or squeezable tube. A clean tip is placed on the dose administration syringe, and the bulk storage syringe, storage container, or squeezable tube is capped and returned to storage until another dose is needed to be administered. The dose administration syringe may be placed on a tray specially prepared for the procedure with all of the necessary equipment and treatment material. After administration of the dosage of the composition to a patient, the dose administration syringe is disposed of as well as all other materials that come in contact with the patient's mouth. Thus, each dose administration syringe and tip used comes from a store of new and unused syringes and tips, eliminating any chance of cross-contamination between patients.

It should also be appreciated that the systems and methods of the invention can also be advantageously used for other medical and household applications. Due to its novel design, the bulk storage and dispensing syringe is easy to manipulate and operate using only one hand. The design of the bulk storage syringe also makes it easy to precisely position or direct a composition expressed from the discharge end and to administer precise amounts of the composition. It should be appreciated by those skilled in the art that the bulk storage syringe could also be advantageously used for direct application of various liquid and viscous materials, including materials that would be ideal for use as a dental or surgical irrigator (e.g., for use in irrigating a mouth, surgical incision, or other location) or other similar applications.

It will be appreciated that the present invention may be embodied in other specific forms without departing from its spirit or essential characteristics. The described embodiments are to be considered in all respects only as illustrative and not restrictive, and the scope of the invention is indicated by the claims rather than by the foregoing description. All changes which come within the meaning and range of equivalency of the claims are to be embraced within their scope.

What is claimed and desired to be secured by United States Patent is:

1. A system for storing in bulk and readily dispensing a dental composition, comprising:
    a. a prefilled bulk storage syringe, comprising:
        i. a storage barrel having an inlet end and a discharge end;
        ii. a storage plunger slidably disposed within the storage barrel; and
        iii. gripping means arcuately disposed on the storage barrel in essentially a semicircle around a portion of the storage barrel so as to form a flange having a finger-retaining surface which extends sufficiently outwardly from the storage barrel so that all finger tips except the thumb of a user's hand rest on the finger-retaining surface and so that the storage barrel is held without placing the barrel between the user's fingers while the plunger is being advanced within the storage barrel so as to dispense the dental composition; and
    b. a dose administration syringe comprising a dose barrel having a discharge end, a dose plunger slidably disposed within the dose barrel, and means for coupling the discharge end of the bulk storage syringe to the discharge end of the dose administration syringe, such that both syringes are in fluid communication with each other for dispensing a single dose of the dental composition from the bulk storage syringe into the dose administration syringe.

2. The system of claim 1, wherein a predetermined distance between the gripping means and the inlet end of the storage barrel allows the fingers of a user to remain in substantial abduction while the storage plunger is advanced toward the discharge end of the storage barrel.

3. The system of claim 1, wherein the bulk storage syringe has an opening in the discharge end of the storage barrel that is sufficiently large to easily dispense a highly viscous material.

4. The system of claim 1, wherein the finger-retaining surface is curved so as to accommodate and retain the user's finger tips placed thereon while the plunger is advanced within the storage barrel.

5. The system of claim 1, wherein the flange having the finger-retaining surface further comprises a first lateral edge located at a first end of the flange, and a second lateral edge located at a second end of the flange, wherein the first and second edges are substantially flat such that the bulk storage syringe will rest on a flat surface without rolling.

6. The system of claim 1, further comprising plunger handle means positioned on the storage plunger for receiving and seating a palm of the hand while the user's finger tips are simultaneously retained by the gripping means.

7. The system of claim 6, wherein the plunger handle means comprises a circular flange formed on a rear end of the storage plunger, the circular flange being sized so as to be capable of being received and seated within the palm of the hand while the user's finger tips are simultaneously retained by the gripping means, whereby a compressive force exerted by the user's fingers and the palm causes the storage plunger to advance within the storage barrel such that the dental composition is dispensed into the dose administration syringe.

8. The system of claim 1, wherein the bulk storage syringe further comprises a threaded portion formed on the discharge end of the bulk storage syringe, and wherein the dose administration syringe comprises a complimentary threaded portion formed on the discharge end of the dose administration syringe which is capable of threadably engaging the threaded portion on the bulk storage syringe.

9. The system of claim 1, wherein the bulk storage syringe further comprises a male Luer connector on the discharge end of the bulk storage syringe, and wherein the dose administration syringe comprises a female Luer connector on the discharge end of the dose administration syringe.

10. The system of claim 1, wherein the storage barrel is sufficiently large for storing multiple doses of the dental composition.

11. The system of claim 1, wherein the storage barrel is at least about one inch in diameter.

12. The system of claim 1, wherein the storage barrel is marked with a plurality of gradients, wherein each gradient represents a single dosage of the dental composition.

13. The system of claim 1, wherein the dose administration syringe is marked with a plurality of gradients, wherein each gradient represents a single dosage of the dental composition.

14. A system for storing in bulk and readily dispensing a dental composition, comprising:

a. a bulk storage syringe comprising:
   i. a cylindrical storage barrel having a discharge end and an inlet end, the storage barrel being of sufficient diameter such that the bulk storage syringe is capable of storing multiple doses of the dental composition;
   ii. a storage plunger slidably received within the storage barrel through the inlet end in an air-tight manner, such that advancement of the storage plunger dispenses the dental composition through the discharge end of the storage barrel;
   iii. a finger flange positioned on the storage barrel and extending outwardly so as to be substantially perpendicular to a surface of the storage barrel thereby forming a single and continuous finger-retaining surface, wherein the finger-retaining surface extends only partially around the circumference of the storage barrel and extends sufficiently outwardly from the storage barrel so as to retain a plurality of a user's finger tips of one hand in an adjacent manner while the storage plunger is being advanced within the storage barrel;
   iv. a circular flange formed on a rear end of the storage plunger, the circular flange being sized so as to be received and seated within a palm of the hand while the user's finger tips are simultaneously retained by the finger-retaining surface, whereby a compressive force exerted by the finger-tips and the palm causes the plunger to advance within the storage barrel without placing the storage barrel between the user's finger tips;
   v. a threaded portion formed on an exterior of the discharge end of the bulk storage syringe; and
b. a dose administration syringe comprising a dose barrel having a discharge end, a dose plunger slidably disposed within the dose barrel, and a threaded portion formed on an interior surface of the discharge end of the dose barrel that can threadably engage the threaded portion formed on the discharge end of the bulk storage syringe.

15. An improved storage syringe for use in a system for storing in bulk and readily dispensing a dental composition, the system including a dose administration syringe adapted for coupling to the storage syringe, the improved storage syringe comprising:
   a. an enlarged storage barrel having a discharge end and an inlet end;
   b. a plunger slidably disposed within the storage barrel;
   c. barrel gripping means, disposed on the storage barrel intermediate the discharge and inlet ends, for retaining a plurality of fingers of one hand while the plunger is being advanced within the barrel so as to dispense the dental composition, the barrel gripping means being disposed at a predetermined distance from the inlet end to allow the plunger to be inserted completely into the syringe barrel while a user's fingers remain in substantial abduction, and said barrel gripping means being disposed around a portion of the storage barrel so as to form a flange having a finger-retaining surface which extends sufficiently outwardly from the storage barrel so that the finger tips of a user rest on the finger-retaining surface and so that the enlarged storage barrel is held without placing the barrel between the user's fingers;
   d. plunger handle means, positioned on the plunger, for receiving and seating the palm of the hand while the user's finger tips are simultaneously retained by the barrel gripping means; and
   e. coupling means positioned at the discharge end for detachably coupling a dose administration syringe.

16. An improved storage syringe for use in a system for storing in bulk and readily dispensing a dental composition, the system including a dose administration syringe adapted for coupling to the storage syringe, and the improved storage syringe comprising:
   a. an enlarged storage barrel having an inlet end and a discharge end;
   b. a plunger slidably disposed within the enlarged storage barrel; and
   c. barrel gripping means arcuately disposed on the storage barrel intermediate the inlet end and discharge end and at a predetermined distance from the inlet end to allow the plunger to be inserted completely into the storage barrel while a user's fingers remain in substantial abduction, and said barrel gripping means being disposed in essentially a semicircle around a portion of the storage barrel so as to form a flange having a finger-retaining surface which extends sufficiently outwardly from the storage barrel so that all finger tips except the thumb of a user's hand rest on the finger-retaining surface and so that the enlarged storage barrel is held without placing the barrel between the user's fingers while the plunger is being advanced within the storage barrel so as to dispense the dental composition, said predetermined distance between the barrel gripping means and the inlet end of the storage barrel being selected in length so as to allow the fingers of a user to essentially always be in substantial abduction when the plunger is withdrawn to its maximum position, and thereafter as the plunger is advanced toward the discharge end of the storage barrel.

17. The system of claim 16, wherein the storage syringe further comprises a threaded portion formed on the discharge end of the storage syringe that is complimentary with a threaded portion formed on the discharge end of the dose administration syringe which is capable of threadably engaging the threaded portion on the storage syringe.

18. The system of claim 16, wherein the storage syringe further comprises a male Luer connector on the discharge end of the storage syringe for coupling with a female Luer connector on the discharge end of the dose administration syringe.

19. The system of claim 16, wherein the storage syringe is sufficiently large for storing multiple doses of the dental composition.

20. The system of claim 16, wherein the dose administration syringe is marked with a plurality of gradients, wherein each gradient represents a single dosage of the dental composition.

21. An improved storage syringe for use in a system for storing in bulk and readily dispensing a dental composition, the system including a dose administration syringe adapted for coupling to the storage syringe, and the improved storage syringe comprising:
   a. a storage barrel having a discharge end and an inlet end;
   b. a plunger slidably disposed within the storage barrel; and
   c. barrel gripping means arcuately disposed on the storage barrel intermediate the discharge and inlet ends at a predetermined distance from the inlet end to allow the plunger to be inserted completely into the storage barrel while a user's fingers remain in substantial abduction, and said barrel gripping means being disposed in essentially a semicircle around a portion of the storage barrel so as to form a flange having a finger-retaining surface which extends sufficiently outwardly from the storage barrel so that all finger tips except the thumb of a user's hand rest on the finger-retaining surface and so that the storage barrel is held without placing the barrel between the user's fingers while the plunger is being advanced within the storage barrel so as to dispense the dental composition.

22. The system of claim 21, wherein the bulk storage barrel further comprises a threaded portion formed on the discharge end of the storage barrel that is complimentary with a threaded portion formed on the discharge end of the dose administrator syringe which is capable of threadably engaging the threaded portion on the storage barrel.

23. The system of claim 21, wherein the bulk storage barrel further comprises a male Luer connector on the discharge end of the storage barrel for coupling with a female Luer connector on the discharge end of the dose administration syringe.

24. The system of claim 21, wherein the storage barrel is sufficiently large for storing multiple doses of the dental composition.

25. The system of claim 21, wherein the dose administration syringe is marked with a plurality of gradients, wherein each gradient represents a single dosage of the dental composition.

* * * * *